United States Patent [19]

Wyatt

[11] Patent Number: 4,910,307

[45] Date of Patent: Mar. 20, 1990

[54] PROCESS FOR PREPARING PURINES

[75] Inventor: Paul G. Wyatt, Epsom, England

[73] Assignee: Beecham Group p.l.c., Middlesex, England

[21] Appl. No.: 260,456

[22] Filed: Oct. 20, 1988

[30] Foreign Application Priority Data

Oct. 22, 1987 [GB] United Kingdom ............... 8724765

[51] Int. Cl.$^4$ ................... C07D 473/18; A61K 31/52
[52] U.S. Cl. ............................. 544/276; 544/277; 544/244
[58] Field of Search ............... 544/276, 277; 514/261, 514/262

[56] References Cited

U.S. PATENT DOCUMENTS 4,701,526 10/1987 Kobe et al. ..................... 544/251

Primary Examiner—Nicholas S. Rizzo
Attorney, Agent, or Firm—Hopgood, Calimafde, Kalil, Blaustein & Judlowe

[57] ABSTRACT

A process for the preparation of compounds of formula (I), and pharmaceutically acceptable salts thereof:

t,0010 wherein
 $R_1$ is hydrogen or $CH_2OH$;
 $R_2$ is hydrogen or, (when $R_1$ is hydrogen), hydroxy or $CH_2OH$;
 $R_3$ is $CH_2OH$ or, (when $R_1$ and $R_2$ are both hydrogen), $CH(OH)CH_2OH$;
 $R_4$ is hydrogen, hydroxy, amino or $OR_5$ wherein
 $R_5$ is $C_{1-6}$ alkyl, phenyl or phenyl $C_{1-2}$ alkyl either of which phenyl moieties may be substituted by one or two halo, $C_{1-4}$ alkyl or $C_{1-4}$ alkoxy groups;
 and in which any OH groups in $R_1$, $R_2$ and/or $R_3$ may be in the form of O-acyl, phosphate, cyclic acetal or cyclic carbonate derivatives thereof;

which process comprises the reaction of a compound of formula (II):

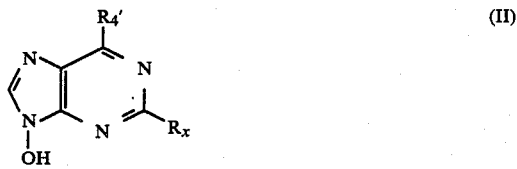

(II)

wherein $R_4'$ is $R_4$ or a group or atom convertible thereto and $R_x$ is amino or protected amino; with a compound of formula (III):

$R_3'CHR_2'CHR_1'Q$     (III)

wherein Q is a leaving group and $R_1'$, $R_2'$ and $R_3'$ are $R_1$, $R_2$ and $R_3$ respectively or $R_1$, $R_2$ and/or $R_3$ wherein the OH group(s) is/are in protected form; and thereafter converting $R_4'$ when other than $R_4$, to an $R_4$ moiety or converting $R_4'$ when $R_4$ to other $R_4$; if necessary converting $R_1'$, $R_2'$ or $R_3'$ to $R_1$, $R_1$ and $R_3$ respectively and optionally forming a pharmaceutically acceptable salt, O-acyl, phosphate, cyclic acetal or cyclic carbonate derivative thereof.

7 Claims, No Drawings

PROCESS FOR PREPARING PURINES

The present invention relates to a novel process for the preparation of compounds having antiviral activity.

EP-A-0242482 describes a class of guanine derivatives having antiviral activity, and processes by which they may be prepared.

A novel process has now been discovered for the preparation of these compounds of formula (I) and pharmaceutically acceptable salts thereof.

Accordingly, the present invention provides a process for the preparation of compounds of formula (I), and pharmaceutically acceptable salts thereof:

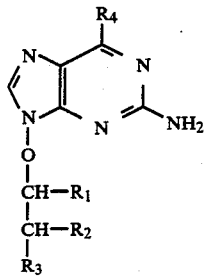

(I)

wherein
- $R_1$ is hydrogen or $CH_2OH$;
- $R_2$ is hydrogen or, (when $R_1$ is hydrogen), hydroxy or $CH_2OH$;
- $R_3$ is $CH_2OH$ or, (when $R_1$ and $R_2$ are both hydrogen), $CH(OH)CH_2OH$;
- $R_4$ is hydrogen, hydroxy, amino or $OR_5$ wherein
- $R_5$ is $C_{1-6}$ alkyl, phenyl or phenyl $C_{1-2}$ alkyl either of which phenyl moieties may be substituted by one or two halo, $C_{1-4}$ alkyl or $C_{1-4}$ alkoxy groups;
- and in which any OH groups in $R_1$, $R_2$ and/or $R_3$ may be in the form of O-acyl, phosphate, cyclic acetal or cyclic carbonate derivatives thereof;

which process comprises the reaction of a compound of formula (II):

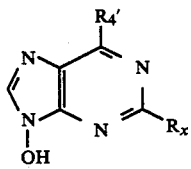

(II)

wherein $R_4'$ is $R_4$ or a group or atom convertible thereto and $R_x$ is amino or protected amino; with a compound of formula (III):

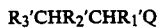

$R_3'CHR_2'CHR_1'Q$ (III)

wherein Q is a leaving group and $R_1'$, $R_2'$ and $R_3'$ are $R_1$, $R_2$ and $R_3$ respectively or $R_1$, $R_2$ and/or $R_3$ wherein the OH group(s) is/are in protected form; and thereafter converting $R_4'$ when other than $R_4$, to an $R_4$ moiety or converting $R_4'$ when $R_4$ to other $R_4$; if necessary converting $R_1'$, $R_2'$ or $R_3'$ to $R_1$, $R_1$ and $R_3$ respectively and optionally forming a pharmaceutically acceptable salt, O-acyl, phosphate, cyclic acetal or cyclic carbonate derivative thereof.

There are groups of compounds within formula (I) as follows:
- (a) $R_1$ and $R_2$ are both hydrogen and $R_3$ is $CH_2OH$, and derivatives thereof as defined;
- (b) $R_1$ is hydrogen and $R_2$ and $R_3$ are both $CH_2OH$, and derivatives thereof as defined;
- (c) $R_1$ is hydrogen, $R_2$ is hydroxy and $R_3$ is $CH_2OH$, and derivatives thereof as defined;
- (d) $R_1$ is $CH_2OH$, $R_2$ is hydrogen and $R_3$ is $CH_2OH$, and derivatives thereof as defined.
- (e) $R_1$ and $R_2$ are both hydrogen and $R_3$ is $CH(OH)CH_2OH$, and derivatives thereof as defined.

Examples of $R_5$ include methyl, ethyl, n- and iso-propyl, phenyl and benzyl optionally substituted by one or two or methyl, ethyl, n- and iso-propyl, methoxy, ethoxy, n- and iso-propoxy, fluoro, chloro, bromo or $CF_3$.

O-Acyl derivatives are normally those wherein one or more of OH groups in $R_1$, $R_2$ and/or $R_3$ form carboxylic ester groups; such as $C_{1-7}$ alkanoyl and benzoyl optionally substituted by one or two $C_{1-4}$ alkyl, $C_{1-4}$ alkoxy, halogen or $CF_3$ groups. Preferably, carboxylic ester groups are $C_{1-7}$ alkanoyl groups, such as acetyl, propionyl, butyryl, heptanoyl and hexanoyl, most preferably acetyl or propionyl.

Examples of phosphate esters of the compounds of formula (I) include those where one of the acyclic —OH groups is replaced by $(HO)_2$—$PO_2$— groups or salts thereof, or where two —OH groups on carbon atoms are replaced by a bridging —O—P(OH)$O_2$— group.

When $R_1$, $R_2$ and $R_3$ together contain more than one OH group, cyclic acetal groups, such as —O—C($C_{1-3}$alkyl)$_2$—O— or cyclic carbonate, such as —O—CO—O— may be formed.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

When the compound of formula (I) contains a phosphate group suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine.

It will be appreciated that some of the compounds of formula (I) have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

It will be further appreciated that, when $R_4$ is hydroxy in formula (I), the compound exists in the preferred tautomeric form of formula (IA):

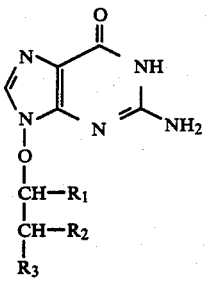

(IA)

The compounds of formula (I) including their alkali metal salts may form solvates such as hydrates and these are included wherever a compound of formula (I) or a salt thereof is herein referred to.

It will also be appreciated that compounds of formula (I) wherein $R_4$ is other than hydroxy are pro-drugs for the compounds of formula (I) wherein $R_4$ is hydroxy.

Suitable values for $R_x$ include amino, when Q is other than hydroxy, or, when Q is hydroxy, $R_x$ is protected amino, such as groups which increase the solubility of the molecule. Preferred examples include carbamates such as ᵗbutyloxycarbonyl, and phthalimide.

Suitable values for Q in formula (III) include hydroxy, halo, such as chloro, bromo and iodo, preferably iodo; or other groups readily displaceable by nucleophile, such as mesyloxy and tosyloxy.

When Q is other than hydroxy, the reaction preferably takes place in an inert solvent, such as dimethylformamide in the presence of a base, such as potassium carbonate, at 0° to 50° C., preferably at ambient temperature.

When Q is hydroxy, the reaction values place in an inert solvent, such as tetrahydrofuran in the presence of a condensation promoting agent, such as diethyl azodicarboxylate (DEAD) and triphenylphosphine at 0° to 50° C., preferably at ambient temperature.

$R_4$ may often be an alkoxy group, such as methoxy, which may be converted to $R_4$ is hydroxy by the methods of D. R. Haines, J. Med. Chem. 1987, 30, 943 and K. K. Ogilvie and H. R. Hanna, Can. J. Chem. 1984, 62, 2702.

When $R_4'$ is chloro, it may be converted to $R_4$, as follows:

(i) Hydrolysis to $R_4$ is hydroxy may be carried out using aqueous mineral acid, such as hydrochloric acid, or more preferably using an organic acid, such as formic acid at elevated temperature, suitably 70°–150° C., preferably 100° C.

(ii) Reduction to $R_4$ is hydrogen, preferably using catalytic methods, such as palladium on charcoal in an inert solvent, such as methanol or ethanol at reflux temperatures. The hydrogen source may be cyclohexene or ammonium formate. The procedure is analogous to of that described by T. A. Krenitsky et.al. Proc. Natl. Acad.Sci. USA. 81, 3209 (1984).

(iii) Conversion to $R_4$ is amino may be achieved conventionally by treatment with ammonia in methanol in an autoclave at 100° C. for a period of about 7 hours, or alternatively, with sodium azide in dimethylformamide to form an azido intermediate (wherein $R_4$ is $N_3$), followed by reduction of this intermediate with ammonium formate/palladium on charcoal, in methanol.

(iv) Reaction with $OR_5^-$ with the resulting chloro compound may be achieved using, preferably, $NaOR_5$ in a suitable solvent, such as methanol or ethanol when $R_5$ is methyl or ethyl respectively, at 0°–150° C., preferably around 50° C. The procedure is analogous to that described in Example 15 of EP-A-141927.

$R_1'$, $R_2'$ and/or $R_3'$ when protected OH groups, the protecting group(s) are often hydrogenolysable such as a benzyl group optionally substituted as defined above for $R_5$ when phenyl, also including nitro as an optional substituent.

Removal of benzyl protecting groups may be achieved conventionally, by catalytic hydrogenation using palladium on charcoal as catalyst (when $R_4$ is other than hydrogen).

Other suitable protecting groups include substituted benzyl groups such as p-methoxybenzyl, removable by treatment with DDQ.

Another suitable protecting group is the ᵗButyl dimethylsilyl group removable by 80% acetic acid at elevated temperatures, around 90° C., or treatment with tetrabutyl ammonium fluoride in a solvent such as tetrahydrofuran, at ambient temperature.

A particularly suitable protecting group is that wherein two OH groups on carbon atoms α- or β- to one another are reacted with 2,2-dimethoxypropane, forming a 1,3-dioxolan or 1,3-dioxan ring respectively. This group may be removed by acidic hydrolysis.

Alternative values for $R_2'$ and $R_3'$, when protected OH groups, include that wherein two OH groups on adjacent carbon atoms are replaced by a bond; for example, when $R_1$ is hydrogen, $R_2$ is hydroxy and $R_3$ is $CH_2OH$; $R_3'CHR_2'CHR_1'O—$ is $CH_2=CH—CH_2—O—$. The diol formation ('deprotection') may be achieved conventionally, for example, using osmium tetroxide, preferably catalytically in the presence of N-methylmorpholine N-oxide.

Pharmaceutically acceptable salts, O-acyl derivatives and phosphate derivatives may be prepared conventionally, for example as described in EP-A-141927 and EP-A-182024.

Acyl derivatives of compounds of formula (I) may be prepared by acylating an optionally protected compound of formula (I) in accordance with conventional acylating processes known in the art, and where necessary, deprotecting the resulting product.

The acylation reaction may be carried out by using an acylating agent containing a suitable carboxylic acid acyl group.

Examples of acylating agents suitable for the above process are carboxylic acids, acid halides, such as chlorides or acid anhydrides, preferably anhydrides or acids.

When the acylating agent is a carboxylic acid, a condensation promoting agent such as dicyclohexylcarbodiimide should be included, but this is not necessary when the acylating agent is an acid anhydride.

The acylation reaction may produce a single acyl derivative of a compound of formula (I), or a mixture of derivatives, depending on a number of factors, such as the relative amounts and chemical natures of reactants, the physical conditions of the reaction, and the solvent system. Any mixture produced in this way may be separated into its pure components using standard chromatographic techniques.

The above described acylation process of the invention can yield mono- or di-acylated derivatives of compounds of formula (I) containing two OH groups, according to the form of protection/deprotection utilised. The following are examples of products obtained by different methods:

(a) Acylated derivatives of the OH groups in R₁/R₂/R₃ when both acyl groups are the same, may be obtained by direct acylation of compounds of formula (I).

(b) Mono-acylated derivatives of one OH group when $R_1$, $R_2$ and $R_3$ together contain two OH groups may be obtained by acylation of protected intermediates of compounds of formula (I) in which the other —OH group in $R_1/R_3/R_3$ is preferably protected by, for example, a monomethoxytrityl or trityl group, and subsequent deprotection by acid treatment. Diacylated derivatives wherein the acyl groups are different may then be prepared as in (a).

Acyl derivatives of the compounds of formula (I) can be converted to a compound of formula (I) by conventional deacylation or partial deacylation processes. For example, reaction with methanolic ammonia can be used to effect complete deacylation to yield a compound of formula (I) wherein both OH groups (when present) are deacylated. Reaction with a mild base such as potassium carbonate can result in partial deacylation of a di-acylated derivative to produce a compound of formula (I) wherein one acyl group and one OH group are present.

Phosphate derivatives are formed by reaction with a phosphorylating agent such as phosphorus oxychloride in pyridine. The NH₂ and any OH groups in $R_1$, $R_2$ and/or $R_3$ are protected as desired or necessary, preferably using a trityl or methoxytrityl protecting group, removable by acid hydrolysis, using acetic acid.

When more than one OH group in $R_1$, $R_2$ and $R_3$ is phosphorylated, a cyclic phosphate derivative is produced with phosphorus oxychloride, when the OH groups are α or β to one another.

Another suitable phosphorylating agent is cyanoethyl phosphoric acid, in which case the product is normally treated with aqueous ammonia, which yields the ammonium salt of the phosphate ester as the final product.

A monophosphate may be converted to a cyclic phosphate using a dehydrating agent, such as dicyclohexylcarbodiimide.

Cyclic acetal derivatives of the compounds of formula (I) may be prepared from the compound of formula (I) wherein two OH groups in the side chain are present, preferably β- to one another, using an acyclic acetal, such as $R_{10}O-C(C_{1-3}alkyl)_2-OR_{10}$ wherein $R_{10}$ is $C_{1-4}$ alkyl, such as methyl or ethyl. The reaction is preferably carried out in an inert solvent such as tetrahydrofuran or dimethylformamide in the presence of an acid such as p-toluenesulphonic acid.

Cyclic carbonate derivatives of the compounds of formula (I) may be prepared from the compound of formula (I), wherein the —NH₂ group is preferably protected; with phosgene or 1,1-carbonyldimidazole, and thereafter deprotecting where necessary. Suitable protecting groups include trityl and monomethoxytrityl. The reaction is preferably carried out in dry pyridine at 0°–50° C., preferably at ambient temperature.

It will be appreciated that conversions of R₄, deprotections and derivative formations may take place in any desired or necessary order.

Compounds of the formula (II) wherein R₄′ is chloro may be prepared by the reaction of a compound of formula (IV):

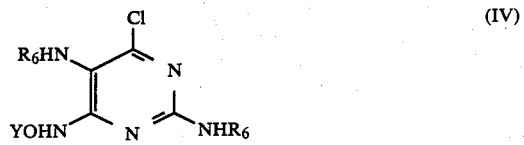

wherein R₆ is formyl, and Y is a protecting group, with diethoxymethyl acetate, giving a compound of formula (V):

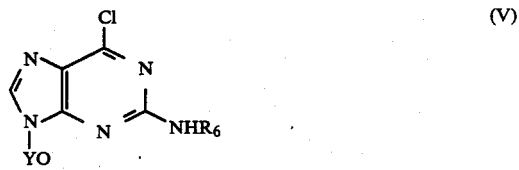

followed by removal of R₆, deprotection of Y and if desired or necessary, converting the 2-amino group to $R_x$ when protected amino and/or converting the chloro substituent to other R₄′.

Suitable values for Y include benzyl, removable by hydrogenation and the tetrahydropyran-2-yl group, removable by treatment with 80% acetic acid, at ambient temperature.

It will be appreciated that the subsequent conversion may take place in any desired or necessary order.

In one aspect, the chloro group is first converted to R₄′ is methoxy, by treatment with methoxide ion (see process iv) as hereinbefore described), then Y, preferably benzyl, is removed.

Compounds of the formula (IV) may be prepared by the reaction of a compound of formula (VI):

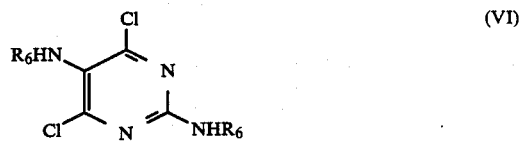

with YONH₂ in an inert solvent, such as dioxan or diglyme in the presence of an acid acceptor, such as triethylamine or diisopropylethylamine.

The above methods are as described in the Example hereinafter.

Intermediates of the formula (II) are novel and form an aspect of the invention.

Intermediates of the formula (III) are known or prepared by methods analogous to those used for the preparation of structurally similar known compounds.

The compound of formula (VI) wherein R₆ is formyl may be prepared by reaction of the corresponding compound of formula (VI) wherein R₆ is hydrogen with formic acid and acetic anhydride.

The compound of formula (VI) wherein R₆ is hydrogen, 2,5-diamino-4,6-dichloropyrimidine is a known compound as described in C. Temple, Jr, B. H. Smith and J. A. Montgomery, J. Org. Chem., 40 (21), 3141, 1975.

The following Examples illustrate the invention.

EXAMPLE 1

(a)  6-Benzyloxyamino-4-chloro-2,5-diformamido-pyrimidine

A mixture of 4,6-dichloro-2,5-diformamido-pyrimidine (1.9 g, 8.09 mmol), benzyloxyamine (1 g, 8.13 mmol), triethylamine (2 ml) and dioxan (20 ml) was stirred at 100° C. for 1 hour. The cooled reaction mixture was filtered and the precipitate collected and washed with dioxan (2×5 ml). The filtrate and washings were combined and evaporated to a syrup. Column chromatography on silica gel (eluted with chloroform-ethanol, 30:1) afforded the title compound (1.2 g, 46%). IR: $\nu_{max}$ (KBr) 3242, 1694, 1588, 1472 cm$^{-1}$; $^1$H NMR $\delta_H$ [(CD$_3$)$_2$SO], 4.89 (2H, s, OCH$_2$Ph), 7.4 (5H, m, Ph), 8.15 (1H, s, CHO), 9.18, 9.42 (1H, 2×br.s, D$_2$O exchangeable, NH), 9.25 (1H, br.s, CHO), 10.91 (2H, br.s, D$_2$O exchangeable, 2×NH). m/e (FAB+ve ion, thioglycerol) MH+ 322.

(b) 9-Benzyloxy-6-chloro-2-formamidopurine

6-Benzyloxyamino-4-chloro-2,5-diformamidopyrimidine (1.2 g, 3.73 mmol) and diethoxymethyl acetate (20 ml) was stirred at 120° C. for 2.5 hours, cooled and evaporated under reduced pressure. The residue in methanol (20 ml) and concentrated ammonia solution (2 ml) was stirred at 20° C. for 1 hour, the solvent removed under reduced pressure and the residue co-evaporated with methanol. Column chromatography on silica gel (eluted with chloroform-ethanol, 100:1) afforded the title compound (700 mg, 62%). IR: $\nu_{max}$ (KBr) 3119, 1702, 1611, 1577, 1505, 1440 cm$^{-1}$; $^1$H NMR: $\delta_H$ [(CD$_3$)$_2$SO], 5.44 (2H, s, CH$_2$Ph), 7.45 (5H, m, Ph), 8.54 (1H, s, H-8), 9.34 (1H, s, CHO), 11.30 (1H, br.s, D$_2$O exchangeable, NH).

Found: C, 49.99; H, 3.37; N, 22.43%, m/e 303.0523. C$_{13}$H$_{10}$N$_5$O$_2$Cl+0.5H$_2$O requires: C, 49.92; H, 3.55; N, 22.40%, m/e 303.0520.

(c) 2-Amino-9-benzyloxy-6-methoxypurine

A mixture of 9-benzyloxy-6-chloro-2-formamidopurine (440 mg, 1.60 mmol), 1.2M sodium methoxide in methanol (5.3 ml) and methanol (10 ml) was heated at reflux temperature for 1 hour and then cooled. Acetic acid (4 ml) was added and the solution evaporated to dryness. The residue was suspended in water and extracted with chloroform (2×25 ml). The combined chloroform extracts were washed with brine, dried (magnesium sulphate) and evaporated under reduced pressure. Column chromatography on silica gel (eluted with chloroform-methanol, 100:1) afforded the title compound (331 mg, 76%). IR: $\nu_{max}$ (KBr) 3480, 3310, 1625, 1585, 1505, 1485, 1460, 1400 cm$^{-1}$; $^1$H NMR: $\delta_H$ [(CD$_3$)$_2$SO] 3.96 (3H, s, CH$_3$), 5.31 (2H, s, CH$_2$Ph), 6.64 (2H, br.s, D$_2$O exchangeable, NH$_2$), 7.42 (5H, s, Ph), 7.75 (1H, s, H-8). Found C, 57.18, H, 4.84; N, 25.85%). m/e 271.1075. C$_{13}$H$_{13}$N$_5$O$_2$ requires: C, 57.56, H, 4.83, N, 25.82%; m/e 271.1069.

(d) 2-Amino-9-hydroxy-6-methoxypurine

A mixture of 2-amino-9-benzyloxy-6-methoxypurine (300 mg, 1.11 mmol), 10% palladium-on-charcoal (100 mg), ethanol (10 ml) and dioxan (5 ml) was stirred under an atmosphere of hydrogen for 45 minutes. The catalyst was then removed and the filtrate evaporated to a white solid 2-amino-9-hydroxy-6-methoxypurine (190 mg, 95%). IR: $\nu_{max}$ (KBr) 3312, 1643, 1591, 1394 cm$^{-1}$; $^1$H NMR: $\delta_H$ [(CD$_3$)$_2$SO] 3.95 (3H, s, CH$_3$), 6.45 (2H, br.s, D$_2$O exchangeable, NH$_2$), 7.93 (1H, s, H-8), 11.75 (1H, br.s, OH). Found: m/e 181.0594. C$_6$H$_7$N$_5$O$_2$ requires: m/e 181.0596.

(e) 2-Amino-9-(2,2-dimethyl-1,3-dioxan-5-ylmethoxy)-6-methoxypurine

A mixture of 2-amino-9-hydroxy-6-methoxypurine (50 mg, 0.276 mmol), 2,2-dimethyl-5-iodo-methyl-1,3-dioxan (70.6 mg, 0.276 mmol), potassium carbonate (40.1 mg, 0.290 mmol) and dimethylformamide (1 ml) was stirred at 20° C. for 3 hours. The suspension was diluted with chloroform (2 ml), filtered and the filtrate evaporated to dryness. The residue was chromatographed on silica gel (eluted with chloroform-ethanol, 100:1) yielding the title compound (59.6 mg, 70%). IR: $\nu_{max}$ (KBr) 3396, 1640, 1581, 1480, 1390 cm$^{-1}$; $^1$H NMR: $\delta_H$ [(CD$_3$)$_2$SO] 1.32 (3H, s, CH$_3$), 1.35 (3H, s, CH$_3$), 2.00 (1H, m, CH), 3.77 (2H, dd, J=11.8, 6.1 Hz, 2×H$_{(ax)}$), 3.96 (3H, s, OCH$_3$), 3.99 (2H, dd, J=11.8, 4.1 Hz, 2×H$_{(eq)}$), 4.36 (2H, d, J=6.8 Hz, CH$_2$ON), 6.60 (2H, br.s, D$_2$O exchangeable, NH$_2$), 8.14 (1H, s, H-8). Found: C, 50.67; H, 6.31; N, 22.00%; m/e 309.1425. C$_{13}$H$_{19}$N$_5$O$_4$+0.2 EtOH requires: C, 50.53; H, 6.41; N, 21.99%; m/e 309.1434.

This compound may be converted to the corresponding compound of formula (I) wherein R$_4$ is hydroxy according to the methods thereinbefore described. Conversion to R$_2$ and R$_3$ are CH$_2$OH may be achieved by conventional hydrolysis.

EXAMPLE 2

(a) 9-Benzyloxy-2-[(bis-t-butoxycarbonyl)amino]-6-methoxypurine

A solution of 2-amino-9-benzyloxy-6-methoxypurine (0.47 g; 1.73 mmol), di-t-butyldicarbonate (0.57 g; 2.60 mmol) and 4-N,N-dimethylaminopyridine (100 mg, 0.173 mmol) in tetrahydrofuran was heated at reflux for 45 minutes. Additional di-t-butyldicarbonate (0.20 g) was then added and the solution refluxed for 30 minutes. The reaction was then cooled and the solvent removed under reduced pressure. The residue was purified by column chormatography on silica gel eluting with chloroform-methanol mixtures, affording the title compound (740 mg; 91%). IR: $\nu$max (KBr) 3110, 2990, 1760, 1600, 1485, 1460, 1400 cm$^{-1}$; $^1$H NMR: $\delta$H(CDCl$_3$) 1.50(18H, s, 6×CH$_3$), 4.15(3H, s, CH$_3$), 5.45(2H, s, CH$_2$), 7.35(5H, s, Ar), 7.65(1H, s, H-8).

(b) 2-[(Bis-t-butoxycarbonyl)amino]-9-hydroxy-6-methoxypurine

A mixture of 9-benzyloxy-2-[(bis-t-butoxycarbonyl)amino]-6-methoxypurine (990 mg; 2.10 mmol), 10% palladium on charcoal (100 mg), ethanol (25 ml) and dioxan (25 ml) was stirred at 20° C. under an atmosphere of hydrogen for 45 minutes. The suspension was then filtered and the filtrate evaporated under reduced pressure. The resulting white solid was dried to yield the title compound (760 mg; 95%). IR: $\nu$max (KBr) 2990, 2420, 1760, 1740, 1730, 1710, 1605, 1480 cm$^{-1}$; $^1$H NMR $\delta$H[(CD$_3$)$_2$SO] 1.40(18H, s, 6×CH$_3$), 4.05(3H, s, OCH$_3$), 8.05(1H, s, H-8), 11.8(1H, br.s, D$_2$O exchangeable, OH). Found: C, 50.27; H, 6.12; N, 17.70%. C$_{16}$H$_{23}$N$_5$O$_6$+0.2EtOH requires: C, 50.42; H, 6.23; N, 17.66%.

(c) 2-[(Bis-t-butoxycarbonyl)amino]-9-(3-t-butyldimethylsilyloxyprop-1-oxy)-6-methoxypurine Diethyl azodicarboxylate (0.62 ml; 3.93 mmol) was added to a solution of 2-[(bis-t-butoxycarbonyl)amino]-9-hydroxy-6-methoxypurine (1.0 g; 2.62 mmol), 3-t-butyldimethylsilyloxypropan-1-ol (0.5 g; 2.62 mmol) and triphenylphosphine (1.03 g; 3.93 mmol) in tetrahydrofuran (20 ml) at 0° C. After 5 minutes at 0° C. the solution was allowed to warm to 20° C. and stirred for a further 2 hours. The solvent was then removed under reduced pressure, and the residue purified by column chromatography on silica gel eluting with hexaneacetone (3:1), affording the title compound (1.3 g, 89%). IR: $\nu$max (film) 2940, 2965, 1795, 1760, 1600, 1475, 1395 cm$^{-1}$; $^1$H NMR $\delta$H[(CD$_3$)$_2$SO] 0.04(6H, s, 2×CH$_3$), 0.85(9H, s, 3×CH$_3$), 1.40(18H, s, 6×CH$_3$), 1.90(2H, quintet, J=6.1, 6.3 Hz, CH$_2$CH$_2$CH$_2$), 3.78(2H, t, J=6.1 Hz, CH$_2$OSi), 4.08(3H, s, CH$_3$), 4.48(2H, t, J=6.3 Hz, CH$_2$ON), 8.74(1H, s, H-8). Found: m/e 554.2993. C$_{25}$H$_{44}$N$_5$O$_7$Si requires: m/e 554.3010.

(d) 9-(3-Hydroxyprop-1-oxy)quanine

A solution of 2-[(bis-t-butoxycarbonyl)amino]-9-(3-t-butyldimethylsilyloxyprop-1-oxy)-6-methoxypurine (1.1 g; 1.99 mmol) and 5N hydrochloric acid (1.19 ml) in ethanol (10 ml) was heated at reflux for 5 hours. The reaction was cooled, evaporated under reduced pressure and the residue co-evaporated with ethanol (×4). The residue was suspended in ethanol-water (1:1; 10 ml) and concentrated aqueous ammonia was added until dissolution had occurred. The solution was filtered and the filtrate left to stand unstoppered to allow the ammonia to evaporate. After 48 hours the resulting solid was collected, washed with water, ethanol and dried to afford the title compound (220 mg; 50%). IR $\nu$max (KBr) 3190, 1720, 1685, 1630, 1605 and 1475 cm$^{-1}$; $^1$H NMR $\delta$H[(CD$_3$)$_2$SO] 1.80(2H, quintet, J=6.3 Hz, CH$_2$CH$_2$CH$_2$), 3.55(2H, quartet, J=5.5, 6.3 Hz, CH$_2$OH), 4.32(2H, t, J=6.3 Hz, CH$_2$ON), 4.57(1H, t, J=5.5 Hz, D$_2$O exchangeable, OH), 6.57(2H, br.s, D$_2$O exchangeable, NH$_2$), 7.91(1H, s, H-8), 10.63(1H, br. s, D$_2$O exchangeable, H-1). Found: C, 41.33; H, 5.20; N, 30.24%. C$_8$H$_{11}$N$_5$O$_3$.0.4H$_2$O requires: C, 41.33; H, 5.13; N, 30.14%.

I claim:

1. A process for the preparation of compounds of formula (I), and pharmaceutically acceptable salts thereof:

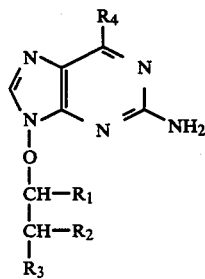

wherein
R$_1$ is hydrogen or CH$_2$OH;
R$_2$ is hydrogen or, (when R$_1$ is hydrogen), hydroxy or CH$_2$OH;
R$_3$ is CH$_2$OH or, (when R$_1$ and R$_2$ are both hydrogen), CH(OH)CH$_2$OH;
R$_4$ is hydrogen, hydroxy, amino or OR$_5$
wherein
R$_5$ is C$_{1-6}$ alkyl, phenyl or phenyl C$_{1-2}$ alkyl either of which phenyl moieties may be substituted by one or two halo, C$_{1-4}$ alkyl or C$_{1-4}$ alkoxy groups;
and in which any OH groups in R$_1$, R$_2$ and/or R$_3$ may be in the form of, C$_{1-7}$ alkanoyl and benzoyl optionally substituted by one or two C$_{1-4}$ alkyl, C$_{1-4}$ alkoxy, halogen or CF$_3$ groups, phosphate, —O—C(C$_{1-3}$ alkyl)$_2$—O—, or —O—CO—O— derivatives thereof;

which process comprises the reaction of a compound of formula (II):

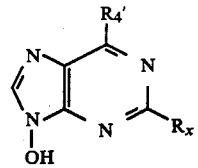

wherein R$_4$′ is R$_4$ or a group or atom convertible thereto and R$_x$ is amino or protected amino; with a compound of formula (III):

wherein Q is a leaving group and R$_1$′, R$_2$′ and R$_3$′ are R$_1$, R$_2$ and R$_3$ respectively, one or more of which may have a protected OH group; and thereafter treating R$_4$′ in a conventional manner to convert R$_4$′ to R$^4$ or, if R$_4$′ is R$_4$, to convert R$_4$′ to another R$_4$; and, if necessary, treating R$_1$′, R$_2$′ or R$_3$′ to form R$_1$, R$_2$ and R$_3$, respectively, and optionally forming a pharmaceutically acceptable salt, phosphate, carboxylic ester, —O—C(C$_{1-3}$ alkyl)$_2$—O—, or —O—CO—O— derivative thereof, according to conventional methods.

2. A process according to claim 1 for the preparation of a compound of formula (I) as defined in claim 1, wherein R$_1$ is hydrogen and R$_2$ and R$_3$ are both CH$_2$OH, and derivatives thereof as defined in claim 1.

3. A process according to claim 1 for the preparation of a compound of formula (I) as defined in claim 1, wherein R$_1$ is hydrogen, R$_2$ is hydroxy and R$_3$ is CH$_2$OH, and derivatives thereof as defined in claim 1.

4. A process according to claim 1 for the preparation of a compound of formula (I) as defined in claim 1, wherein R$_1$ is CH$_2$OH, R$_2$ is hydrogen and R$_3$ is CH$_2$OH, and derivatives thereof as defined in claim 1.

5. A process according to claim 1 for the preparation of a compound of formula (I) as defined in claim 1, wherein R$_1$ and R$_2$ are both hydrogen and R$_3$ is CH(OH)CH$_2$OH, and derivatives thereof as defined in claim 1.

6. A process according to claim 1 for the preparation of a compound of formula I as defined in any one of claims 2 to 5 wherein OH groups in R$_1$, R$_2$, and/or R$_3$ are in the form of an acetate, hexanoate or benzoate derivative thereof.

7. A process according to claim 1 for the preparation of a compound of formula (I) which is:
9-(3-hydroxyprop-1-oxy)guanine,
9-(3-acetoxyprop-1-oxy)guanine,
9-(3-benzoyloxyprop-1-oxy)guanine,
2-amino-6-ethoxy-9-(3-hydroxyprop-1-oxy)purine,
9-(3-hydroxy-2-hydroxymethylprop-1-oxy)guanine,
9-(2,3-dihydroxyprop-1-oxy)guanine,
2-amino-9-(2,3-dihydroxyprop-1-oxy)purine,
9-(1,4-dihydroxybut-2-oxy)guanine,
2-amino-9-(1,4-dihydroxybut-2-oxy)purine,
2-amino-9-(3-hydroxyprop-1-oxy)purine,
9-(3-hexanoyloxyprop-1-oxy)guanine,
2-amino-9-(1,4-diacetoxybut-2-oxy)purine,
2-amino-9-(1,4-dibutyryloxybut-2-oxy)purine,
(R)-9-(1,4-dihydroxybut-2-oxy)guanine,
(S)-9-(1,4-dihydroxybut-2-oxy)guanine, 2-amino-9-(3-hydroxy-2-hydroxymethylprop-1-oxy)purine,
9-(3-acetoxy-2-acetoxymethylprop-1-oxy)-2-aminopurine,
2-amino-9-(3-propionyloxy-2-propionyloxymethylprop-1-oxy)purine,
2-amino-9-(3-benzoyloxy-2-benzoyloxymethylprop-1-oxy)purine,
2-amino-9-(3-hydroxy-2-hydroxymethylprop-1-oxy)-6-methoxypurine,
2,6-diamino-9-(3-hydroxy-2-hydroxymethylprop-1-oxy)purine,
9-(3-acetoxyprop-1-oxy)-2-aminopurine,
2-amino-9-(3-hexanoyloxyprop-1-oxy)purine,
2-amino-9-(3-benzoyloxyprop-1-oxy)purine,
(S)-9-(1,4-diacetoxybut-2-oxy)guanine,
2-amino-9-(2,3-dihydroxyprop-1-oxy)-6-methoxypurine,
(R)-9-(2,3-dihydroxyprop-1-oxy)guanine,
9-(3,4-dihydroxybut-1-oxy)guanine,
2-amino-9-(3,4-dihydroxybut-1-oxy)purine,
(R)-2-amino-9-(2,3-dihydroxyprop-1-oxy)purine,
(S)-9-(2,3-dihydroxyprop-1-oxy)guanine or
(S)-2-amino-9-(2,3-dihydroxyprop-1-oxy)purine.

* * * * *